United States Patent [19]

Ternström et al.

[11] Patent Number: 5,004,465
[45] Date of Patent: Apr. 2, 1991

[54] DISPOSABLE ABSORBENT ARTICLE

[75] Inventors: Ingela Ternström, Mölnlycke; Mats Eriksson, Vastra Frölunda, both of Sweden

[73] Assignee: Molnlycke AB, Gothenburg, Sweden

[21] Appl. No.: 377,856

[22] PCT Filed: Jan. 18, 1988

[86] PCT No.: PCT/SE87/00009

§ 371 Date: Jun. 21, 1989

§ 102(e) Date: Jun. 21, 1989

[87] PCT Pub. No.: WO88/05269

PCT Pub. Date: Jul. 28, 1988

[30] Foreign Application Priority Data

Jan. 19, 1987 [SE] Sweden .................................. 8700179

[51] Int. Cl.⁵ .............................................. A61F 13/16
[52] U.S. Cl. ................................. 604/385.1; 604/365; 604/378; 604/382
[58] Field of Search ............. 604/365, 378, 382, 385.2

[56] References Cited

U.S. PATENT DOCUMENTS

| | | | |
|---|---|---|---|
| 3,498,296 | 3/1970 | Gallagher | 604/377 |
| 3,949,130 | 4/1976 | Sabee et al. | 604/365 |
| 4,055,180 | 10/1977 | Karami | 604/368 |
| 4,573,986 | 3/1986 | Minetola et al. | 604/366 |
| 4,775,375 | 10/1988 | Aledo | 604/385.2 |
| 4,795,451 | 1/1989 | Buckley | 604/385.2 |
| 4,897,084 | 1/1990 | Ternstroröm et al. | 604/385.2 |

FOREIGN PATENT DOCUMENTS

| | | |
|---|---|---|
| 0059015 | 9/1982 | European Pat. Off. . |
| 0176305 | 4/1986 | European Pat. Off. . |
| 2714552 | 11/1977 | Fed. Rep. of Germany . |
| 3244234 | 8/1983 | Fed. Rep. of Germany . |
| 2583620 | 12/1986 | France . |
| 453880 | 3/1988 | Sweden . |

*Primary Examiner*—Stephen C. Pellegrino
*Assistant Examiner*—Gary Jackson
*Attorney, Agent, or Firm*—Young & Thompson

[57] ABSTRACT

A disposable absorbent article such as a diaper, a sanitary napkin, an incontinence protection garment, a wound dressing or the like has a liquid impermeable surface layer (2) and a liquid permeable surface layer (4) encasing an absorbent core (5) therebetween, and elastic members (11–14) applied thereto. The liquid permeable layer (4) is composed of at least two separate webs (3, 4) joined together by a bonding pattern constituted by substantially parallel bonding lines at least crossing the elastic members (11–14) in order to cooperate with these members, whereby the liquid permeable surface layer (4) on its side turned away from the absorbent core (5) air-filled channels and a soft, wavy surface.

9 Claims, 3 Drawing Sheets

DISPOSABLE ABSORBENT ARTICLE

FIELD OF THE INVENTION

The present invention relates to a disposable absorbent article such as a diaper, a sanitary napkin, an incontinence protection garment, a wound dressing or the like comprising a liquid impermeable surface layer and a liquid permeable surface layer encasing an absorbent core therebetween.

BACKGROUND OF THE INVENTION

Up to now, the liquid permeable surface layer of such articles has generally been composed of a fiber fabric web. Preferably, a web of this type should have no liquid absorbency but should only be capable of permitting the flow of fluid into the absorbent core accommodated inside it. Furthermore, the liquid permeable surface layer constituting the web facing the wearer's skin during use of the article should preferably be made soft, smooth and airy although with a sufficient degree of tensile strength.

The important demand on such a body-contacting diaper surface layer to be soft, airy and non-irritating to the wearer's skin has been recognized since long, for example through the European patent application No. 0 059 498 teaching an absorbent article with a liquid permeable surface layer consisting of a laminate composed of two different webs of which one is made from unbonded thermoplastic fibers and the other from a fiber fabric or net for example, constituting a web serving to support the first-mentioned layer. The thermoplastic fibers in the first-mentioned layer are melt bonded to the other layer or supporting web, preferably in a bonding pattern formed of crossing lines creating a diamond pattern. The purpose of such a laminate is to accomplish a soft body contacting surface layer without skin irritating effects, promoting simultaneously a rapid throughflow of body fluids into the absorbent core of the article.

The tensile strength of an unbonded fibrous layer is however known to be extremely poor even when bonded to a supporting web as is the case with the aforementioned prior art laminate. The risk of tearing or shedding fibers associated with this type of material is obvious unless, as a precaution, the bonding pattern for the supporting web is given a sufficiently close structure. The closer the bonding pattern, the stiffer, more awkward and less liquid impermeable the laminated surface layer thereby making it unsuitable for its purpose.

The handling and transport problems associated with unbonded fiber web are additional disadvantages in the manufacture of absorbent articles such as diapers.

The most common absorbent material used for absorbent products of the diaper type is so-called cellulose fluff pulp consisting of numerous short fibers which for obvious reasons are difficult to keep together into a coherent absorbent core. This factor is most crucial during mechanical treatment of the fibers. When using a disposable diaper with an absorbent core made of cellulose fluff pulp, the absorbent core is for example liable to burst causing the fibers included therein to lump and leaving in this manner large portions of the diaper completely void of absorbent material. This unfortunate effect of the low cohesiveness in cellulose fluff pulp fibers is generally most noticeable in the diaper crotch portion, that is the region of the diaper intended during use to be applied between the wearer's legs, which is the area exposed to maximum mechanical stress occurring in response to the movements of the wearer. This is also the area receiving the major part of urine discharged during use of the diaper. The fact that the absorbent material tends to burst most often in this specific area thus constitutes a serious drawback.

In order to stabilize and strengthen such absorbent cores for increasing their cohesivity during use there is previously known the technique of gluing the two surface layers encasing the absorbent core directly onto the absorbent material. Gluing in this manner can be performed for example by spraying or extruding a thin latticed layer of hot melt adhesive over the absorbent core or the surface layers prior to uniting them.

By gluing the liquid permeable surface layer to the absorbent core there is further provided a close contact between the surface layer and the absorbent core increasing in this manner the speed at which the body fluid enters the absorbent core since the body fluid is then immediately sucked up by the absorbent material substantially unimpeded by the surface layer.

However, as a result of the close relationship between the liquid permeable surface layer and the absorbent core, the body fluid contained in the absorbent core will come in direct contact, via the surface layer, with the diaper surface facing the wearer's body, which is a most significant drawback. As a consequence, the diaper surface layer will feel wet to the wearer when the absorbent core is soaked. In addition, the more or less intimate contact between the wet surface layer and the wearer's skin will prevent this area from being sufficiently ventilated. The tight fit of the absorbent core to the wearer's skin and the poor ventilation possibilities are factors which will finally increase the risk of chafing and skin irritation. Because of the humidity prevailing underneath the diaper due to discharge of urine and transpiration, the skin will moisten making it extremely sensitive to redness and irritation when exposed to mechanical forces. Skin irritation easily occurs especially as a result of chafing and poor ventilation in diapers provided with elastic members sealing tightly around the wearer's thighs. The elastic members of such diapers are generally applied to either side of the absorbent core and are fixed by gluing between the diaper surface layers which are joined together beyond the longitudinal edges of the absorbent core. In order to prevent the absorbent material from forcing its way out between the two surface layers, these layers must be fully glued together by means of hot melt adhesive for example, as hereinbefore described. However, such gluing will make the diaper edges rather stiff thereby creating sharp and chafing pleats at the location of the elastic members.

Accordingly, it has been found difficult so far to achieve a liquid permeable surface layer for absorbent articles with a satisfactory function in all respects. The more or less contradictory demands placed on such a layer with regard to softness, smoothness, surface dryness, airiness and strength are difficult to fulfill with the use of one and the same material, as appears from the foregoing. In case the liquid permeable surface layer also has to be secured to the absorbent core for the reinforcement thereof, and in order to provide for satisfactory liquid transport into it, the demands on user's comfort have not been possible to meet until now.

SUMMARY OF THE INVENTION

With the present invention, however, there has been accomplished a disposable absorbent article of the kind mentioned in the introduction and by means of which the above-stated problems have been overcome.

An article performed according to the invention is primarily distinguished in that the liquid permeable layer is composed of at least two separate webs of identical or different materials, and that these two webs of material are joined together by means of a comparatively open bonding pattern.

The result obtained is a surprisingly high degree of softness in the surface material. In fact, bonding with the use of a relatively open bonding pattern has shown to give the material web a space structure creating a surface layer which is not only soft but also airy.

In a particularly suitable embodiment of an article made in accordance with the invention, the liquid permeable material web lying next to the absorbent core is affixed to the absorbent core by means of a relatively close bonding pattern, producing in this manner a reinforcement of the absorbent core as well as a satisfactory transport of liquid into it.

In another embodiment of an article according to the invention, which is particularly usefor for a disposable diaper having elastic members applied in the transverse and/or longitudinal direction of the diaper and with the liquid permeable and the liquid impermeable layers extending beyond the absorbent core, the liquid permeable material web lying closest to the absorbent core and the liquid impermeable layer are joined together around the periphery of the diaper, the portions of the elastic members disposed beyond the absorbent core being applied between the liquid impermeable layer and the liquid permeable material web joined thereto and the remaining portions of the elastic members being connected solely to the last-mentioned material web.

If the elastic members are secured to the innermost liquid permeable material web, a more obvious formation of pleats will take place in the outermost material web, the size and frequency of said pleats being determined by the tension of the elastic members and the structure of the bonding pattern between the liquid permeable material webs. An open bonding pattern between the liquid permeable material webs in combination with the elastic members thus constitutes a particularly advantageous solution due to the possibility of being able to conveniently control the degree of softness and airiness in the material web facing the wearer's skin.

In a further embodiment of the inventive article, the liquid permeable material webs are joined together by means of a bonding pattern formed of continuous, substantially parallel lines.

However, the liquid permeable material webs could to advantage also be united by means of a bonding pattern constituting broken, substantially parallel lines.

The liquid permeable material web placed most closely to the absorbent core is suitably affixed to this core by means of hot melt adhesive.

The liquid permeable material webs are suitably joined together by extrusion gluing using hot melt adhesive, the bonding lines preferably being spaced apart more than 10 mm but less than 30 mm.

In a likewise suitable embodiment of an article according to the invention, the liquid permeable material web lying closest to the absorbent core consists of a melt bond type fiber fabric layer made of hydrophobic or non-absorbent fibers, whereas the outermost liquid permeable material web consists of a thin spun bond type fiber fabric layer similarly made of hydrophobic or non-absorbent fibers, the last-mentioned web having a lower surface weight than the first-mentioned material web.

With the use of two separate webs of material when building up the liquid permeable surface layer instead of one, which has been the prevailing method up to now, there is gained a plurality of additional advantages apart from those already mentioned.

For example, the risk of rewetting from the absorbent core to the wearer is almost totally eliminated. The reason is firstly, that the double webs will provide for more space and air between the absorbent core and the wearer's skin, and secondly, that the material in the two webs could be chosen so as to allow for the ideal combination of qualities. It may for example be possible to utilize a material with a higher degree of hydrophobicity in the outer than in the inner web, obtaining thereby a "non-return valve effect" resulting in the retention of fluid taken up by the absorbent core.

By selecting a material with high volume per unit of weight for the inner liquid permeable web, this web will be given enhanced airiness and higher liquid insulation capacity. For diapers with elasticized leg cuffs there is also provided a certain degree of padding over the elastic threads, which is an advantage.

BRIEF DESCRIPTION OF THE DRAWINGS

These and other features and advantages of an article performed according to the invention will be elucidated in more detail below with reference to an embodiment illustrated in the accompanying drawings, of which

DETAILED DESCRIPTION OF THE INVENTION

Figure 1:
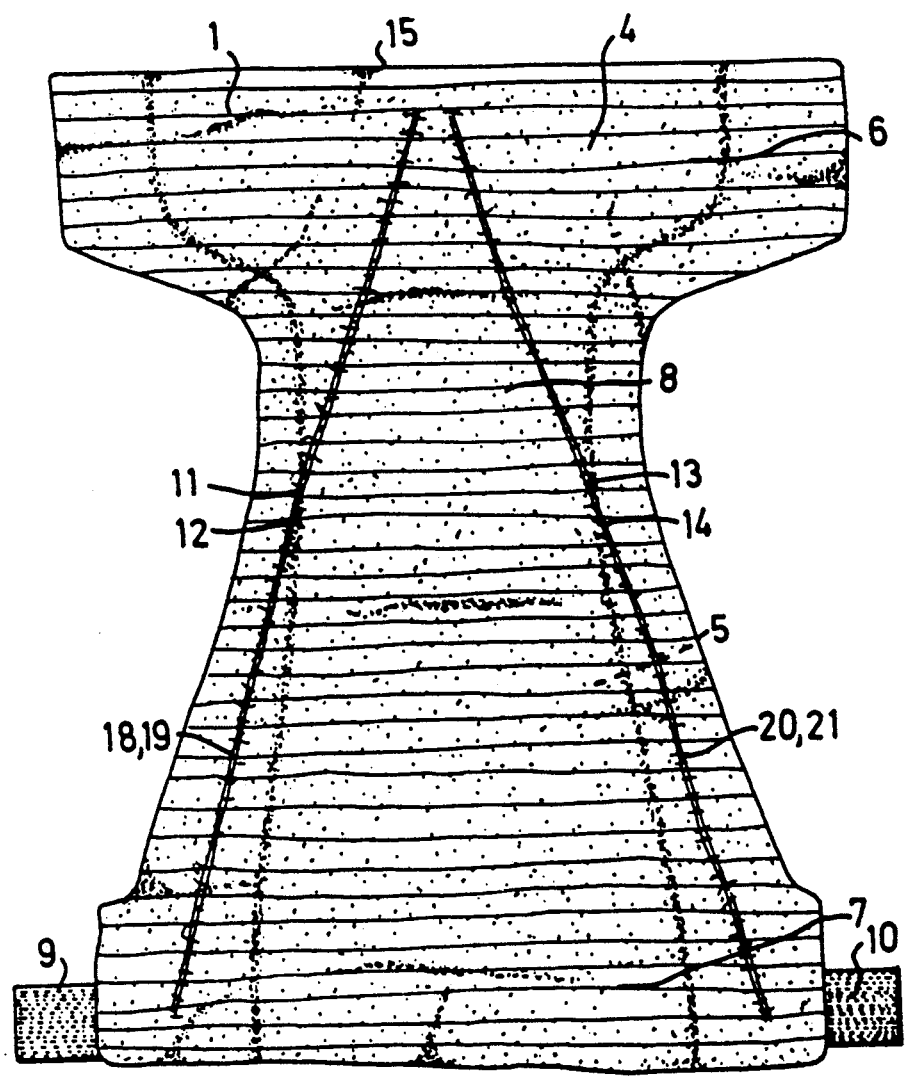
FIG. 1 is a plan view of a diaper performed according to the invention as viewed from the side facing the wearer during use of the diaper.
Figure 2:
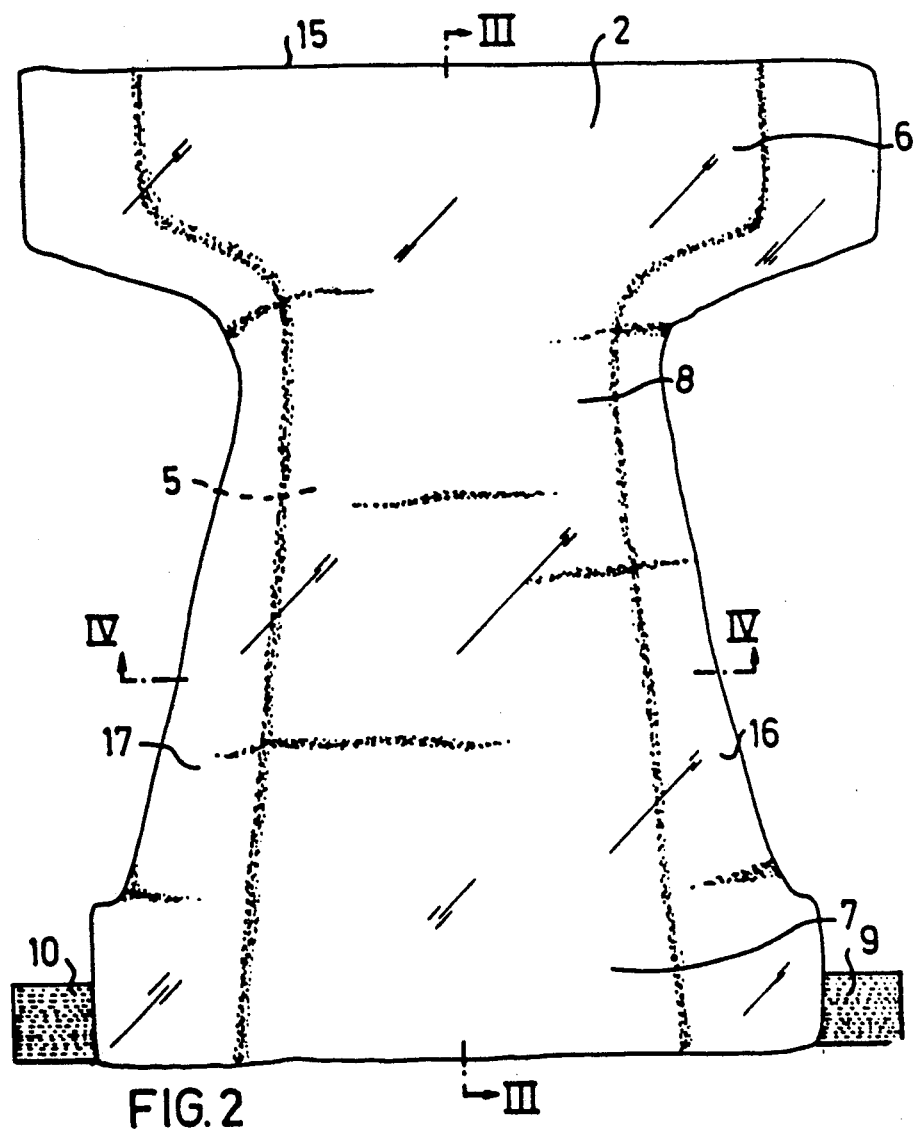
FIG. 2 is a plan view of the diaper shown in FIG. 1 as viewed from the side facing away from the wearer during use of the diaper.

The inventive diaper 1 illustrated in the drawings comprises a liquid tight plastic film 2 disposed on the side of the diaper facing away from the wearer during use, two liquid permeable fiber fabric webs 3, 4 on the side of the diaper facing the wearer during use, and an absorbent core 5 of cellulose fluff pulp encased between the fiber fabric webs 3, 4 and the plastic layer 2.

The diaper 1 further exhibits a wide so-called belly portion 6 intended during use of the diaper 1 to be placed over the wearer's belly, a wide so-called back portion 7 intended during use of the diaper to be placed over the wearer's seat, as well as a narrow so-called crotch portion 8 disposed between the belly portion 6 and the back portion 7 and intended for placement in the crotch region between the wearer's legs during use of the diaper.

The diaper 1 is intended during use to seal around the wearer's abdomen in a pant-like manner for which purpose it is provided with tape tabs 9, 10 serving to secure the diaper back portion 7 to the belly portion 6.

In order to secure a good seal around the wearer's thighs, the diaper 1 is also provided with elastic threads 11-14 forming a V-shaped pattern having its apex at the midpoint of the waist edge 15 of the belly portion. Within the diaper belly portion 6, the elastic threads 11-14 are fixedly glued between the absorbent core 5 and the two liquid permeable fiber fabric webs 3, 4 whereas in the diaper back portion 7 said elastic threads 11-14 extend beyond and along either side of the absorbent core 5 while being glued between the liquid impermeable plastic film 2 and the two liquid permeable fiber fabric webs 3, 4.

The fiber fabric web 3 lying closest to the absorbent core 5 is glued to the absorbent core 5 utilizing a technique by means of which hot melt adhesive is extruded over the fiber fabric web 3 as a thin film which is then stretched out to crack, leaving as a result a net-like, fine-meshed structure providing in this manner a good seal between the surfaces glued together, without blocking the flow of fluid into the absorbent core 5. The innermost fiber fabric web 3 extends alongside the diaper 1 beyond the absorbent core 5 where it is glued to portions 16, 17 of the liquid impermeable plastic film 2, which portions extend beyond the absorbent core 5. The portions 18-21 of the elastic threads 11-14 extending beyond the absorbent core 5 are glued between the plastic film 2 and the innermost fiber fabric web 3.

The technique of gluing employed provides a close contact and a most effective fixture between the absorbent core 5 and the innermost fiber fabric web 3 glued thereto. There is thus obtained the desired stabilization and reinforcement of the absorbent core 5 against disintegration during use of the diaper. Simultaneously, the liquid impermeable film 2 and the inner fiber fabric web 3 together form a casing enclosing the absorbent core 5 so that any absorbent material therefrom will be prevented by the casing from forcing its way out of the diaper.

Figure 3:
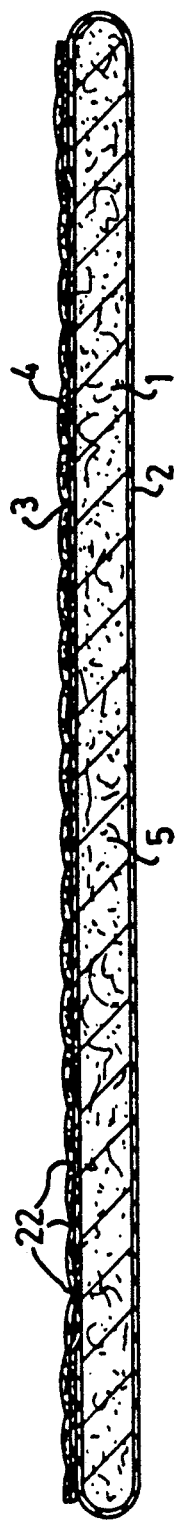
FIG. 3 is a longitudinal sectional view taken along the line III—III through the diaper of FIG. 2; whereas finally
Figure 4:
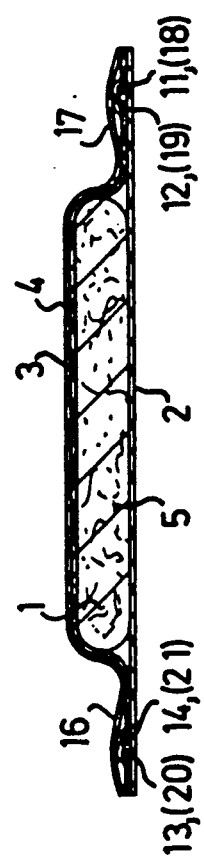
FIG. 4 is a cross sectional view taken along the line IV—IV through the diaper of FIG. 2.

As is best shown in FIGS. 1 and 3, the other liquid permeable fiber fabric web 4 is applied by means of glue beads 22 onto the outside of the innermost fiber fabric web 3 lying closest to the absorbent core 5, which will give the diaper an airy, pleasant and somewhat wavy structure making it very soft but yet strong.

The fact that the outermost fiber fabric web 4 is glued to the innermost web 3 with relatively widely spaced glue beads 22 which also extend over the portions 18-21 of the elastic threads 11-14 disposed at the diaper side edges furthermore renders the diaper edge surprisingly soft and airy. Instead of presenting a multitude of thin, sharp and chafing pleats around the elastic members, as is the case with the majority of conventional diapers having elasticized leg cuffs, the body-contacting surface of a diaper 1 made according to the invention exhibits a bubble-like and very soft structure. With the elastic threads 11-14 unstretched or only moderately stretched, the diaper leg linings are contracted. After gluing, the outer fiber fabric web 4 will bulge from the inner fiber fabric web 3 between the glue beads 22 creating thereby the formation of air-filled channels between the two webs 3, 4 which will allow for the passage of air to the wearer's skin during use of the diaper. The combination of a soft body contacting surface and good ventilation is a factor substantially reducing the risk of chafing and other types of skin irritation when using the diaper.

In order for the elastic threads 11-14 to make the glued outer fiber fabric web bulge as desirable, these threads must be crossed by the glue beads 22. In this manner the glued outer fiber fabric web 4 will be attached to the elastic threads 11-14 at a number of spaced points. Since gluing in beads takes place with the elastic threads 11-14 in a prestretched condition, they will contract on release of the tension, the distance between the fixing points to the glued outer fiber fabric web thereby decreasing. As a result, this web will bulge between its fixing points thus giving the diaper 1 its desired wavy surface.

Attempts with varying distances between the glue beads 22 have shown that optimal coaction between the elastic threads 11-14 and the glue beads is reached when the glue beads are spaced apart more than 10 mm but less than 30 mm.

For the sake of further enhancing the softness of the liquid permeable surface layer of the diaper 1, it would of course be possible to use a loosely bonded inner material web 3 since no substantial strength is required therefor. As a material for the outer web 4, however, a thin, smooth fabric with low skin friction and high strength should be chosen.

In order to make the liquid permeable body contacting surface layer 4 of the diaper 1 feel dry to the wearer even on the absorption of substantial volumes of fluid, at least the outer 4 of the liquid permeable surface layers 3, 4 must be prevented from absorbing any appreciable amount of fluid, permitting only the flow of fluid into the absorbent core 5. This also prevents the migration of fluid in the diaper surface layer 4 causing leakage out past the elastic threads 11-14 at the diaper leg cuffs.

As a material for the inner fiber fabric web 3 it has been found suitable to use spun laced fiber fabric or a carded, melt bonded fiber web with 4–10% bonded surface, melt bonding then being carried out by means of calendering or by treating the carded fibrous web with hot air.

A suitable material for the outer fiber fabric web 4 would be a melt bonded or spun bonded fiber fabric with 15–20% bonded surface. The material in such a layer could be a polypropylene, or a mixture of polyethylene and polypropylene.

The invention is not restricted to the exemplary embodiment described above since a plurality of modifications are conceivable within the scope of the patent claims.

For example, the invention is not limited to the use of two liquid permeable layers since in certain cases the use of three or more similar layers could be preferred.

It is not necessary for the different layers to have identical extensions. In certain cases, for example, it is sufficient for the inner layer to extend over the crotch portion of a diaper.

The invention has been described above with reference to an exemplary embodiment relating to a diaper with V-shaped elastic means. The inventive idea naturally encompasses further embodiments of absorbent articles with or without elastic means which could be applied in any other manner than that disclosed hereinbefore such as, for example, in the transverse direction of the article.

We claim:

1. In a disposable absorbent article such as a diaper, a sanitary napkin, an incontinence protection garment, a wound dressing or the like comprising a liquid impermeable surface layer (2) and a liquid permeable surface layer (4) encasing an absorbent core (5) therebetween, and having elastic members (11-14) applied thereto; the improvement wherein the liquid permeable layer (4) is composed of at least two separate webs (3,4), said at least two webs (3,4) being joined together by means of a bonding pattern constituted by substantially parallel bonding lines at least crossing the elastic members (11-14) in order to cooperate with these members, whereby the liquid permeable surface layer (4) on its side turn away from the absorbent core (5) has air-filled channels and a soft, wavy surface.

2. An article according to claim 1, wherein the liquid permeable material webs (3,4) are joined together by means of hot melt adhesive applied in the form of glue beads.

3. An article according to claim 2 wherein the mutual distance between beads (22) is greater than 10 mm but less than 30 mm.

4. An article according to claim 1, wherein the liquid permeable material web (3) lying closest to the absorbent core is affixed to the absorbent core (5) by means of hot melt adhesive.

5. An article according to claim 1 wherein the liquid permeable surface layer (4) includes, in the following order starting from the absorbent core, a fiber fabric web, a perforated plastic film and an additional fiber fabric web.

6. An article according to claim 1 wherein the liquid permeable material web (3) lying closest to the absorbent core (5) consists of a melt bond type fiber fabric layer made of non-absorbent fibers, and that the outermost liquid permeable material web (4) consists of a thin layer of spun bond type fiber fabric likewise made of non-absorbent fibers, the last-mentioned material web having a lower surface weight than the first-mentioned material web (3).

7. An article according to claim 1 in the form of a disposable diaper (1) having elastic members (11-14) the liquid permeable layer (3,4) and the liquid impermeable layer (2) extending beyond the absorbent core (5), wherein the liquid permeable material web (3) lying closest to the absorbent core (5) and the liquid impermeable layer (2) are joined together around the periphery of the diaper (1), portions (18-21) of the elastic members (11-14) disposed beyond the absorbent core (5) being applied between the liquid impermeable layer (2) and the liquid permeable material web (3) joined thereto, and remaining portions of the elastic members (11-14) being connected only to the last-mentioned material web (3).

8. An article according to claim 7, wherein the liquid permeable surface layer (4) includes, in the following order starting from the absorbent core, a fiber fabric web, a perforated plastic film and an additional fiber fabric web.

9. An article according to claim 1, wherein the liquid permeable material web (3) lying closest to the absorbent core (5) consists of a melt bond type fiber fabric layer made of non-absorbent fibers, and the outermost liquid permeable material web (4) consists of a thin layer of spun bond type fiber fabric likewise made of non-absorbent fibers, the last-mentioned material web having a lower surface weight than the first-mentioned material web (3).

* * * * *